(12) United States Patent
Shiratani

(10) Patent No.: US 10,360,474 B2
(45) Date of Patent: Jul. 23, 2019

(54) IMAGE PROCESSING DEVICE, ENDOSCOPE SYSTEM, AND IMAGE PROCESSING METHOD

(71) Applicant: OLYMPUS CORPORATION, Hachioji-shi, Tokyo (JP)

(72) Inventor: Fumiyuki Shiratani, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 105 days.

(21) Appl. No.: 15/366,803

(22) Filed: Dec. 1, 2016

(65) Prior Publication Data

US 2017/0083791 A1 Mar. 23, 2017

Related U.S. Application Data

(63) Continuation of application No. PCT/JP2015/064450, filed on May 20, 2015.

(30) Foreign Application Priority Data

Jun. 24, 2014 (JP) ................. 2014-129068

(51) Int. Cl.
G06K 9/00 (2006.01)
G06K 9/62 (2006.01)
(Continued)

(52) U.S. Cl.
CPC ........ G06K 9/6212 (2013.01); A61B 1/00009 (2013.01); A61B 1/041 (2013.01);
(Continued)

(58) Field of Classification Search
None
See application file for complete search history.

(56) References Cited

U.S. PATENT DOCUMENTS

| 9,655,593 B2 * | 5/2017 | Kawashima | ......... A61B 8/5207 |
| 2002/0012467 A1 * | 1/2002 | Shiratani | ............. G06K 9/6255 382/224 |

(Continued)

FOREIGN PATENT DOCUMENTS

| JP | 11099127 A | 4/1999 |
| JP | 2004321603 A | 11/2004 |

(Continued)

OTHER PUBLICATIONS

Lee, J., Oh, J., Shah, S. K., Yuan, X., & Tang, S. J. (Mar. 2007). Automatic classification of digestive organs in wireless capsule endoscopy videos. In Proceedings of the 2007 ACM symposium on Applied computing (pp. 1041-1045). ACM.*

(Continued)

Primary Examiner — Samah A Beg
(74) Attorney, Agent, or Firm — Holtz, Holtz & Volek PC

(57) ABSTRACT

An image processing device includes a processor including hardware. The processor implements an image acquisition process that acquires time-series images that were captured in time series, and a process that detects a change position, the change position being a position at which an object captured within the time-series images changes from a first object to a second object. The processor implements the process that extracts a feature quantity from each of the time-series images, determines whether the object captured within each of the time-series images is the first object or the second object based on the feature quantity, extracts candidate positions for the change position based on the determination results, and compares the candidate positions based on the determination results to determine the change position.

11 Claims, 13 Drawing Sheets

(51) Int. Cl.
*G06T 7/73* (2017.01)
*G06T 7/00* (2017.01)
*G06T 7/246* (2017.01)
*A61B 1/00* (2006.01)
*A61B 1/04* (2006.01)
*G06K 9/46* (2006.01)
*G06T 7/254* (2017.01)
*G06K 9/66* (2006.01)
*H04N 5/225* (2006.01)

(52) U.S. Cl.
CPC ....... *G06K 9/00624* (2013.01); *G06K 9/4642* (2013.01); *G06T 7/248* (2017.01); *G06T 7/254* (2017.01); *G06T 7/73* (2017.01); *G06T 7/97* (2017.01); *G06K 9/66* (2013.01); *G06T 7/0012* (2013.01); *G06T 2207/10016* (2013.01); *G06T 2207/10068* (2013.01); *H04N 2005/2255* (2013.01)

(56) References Cited

U.S. PATENT DOCUMENTS

| | | | |
|---|---|---|---|
| 2004/0249291 A1* | 12/2004 | Honda | A61B 1/00009 600/476 |
| 2007/0165932 A1* | 7/2007 | Nishimura | A61B 1/00016 382/128 |
| 2008/0119691 A1* | 5/2008 | Yagi | A61B 1/00009 600/109 |
| 2008/0279431 A1* | 11/2008 | Kitamura | A61B 1/00009 382/128 |
| 2009/0010551 A1* | 1/2009 | Matsuda | A61B 1/041 382/228 |
| 2009/0163812 A1 | 6/2009 | Chouno | |
| 2009/0208071 A1* | 8/2009 | Nishimura | A61B 1/041 382/128 |
| 2010/0097401 A1* | 4/2010 | Shiratani | G09G 5/00 345/660 |
| 2010/0194869 A1* | 8/2010 | Matsuzaki | G06T 7/254 348/65 |
| 2010/0208047 A1* | 8/2010 | Kitamura | A61B 1/041 348/65 |
| 2010/0272358 A1* | 10/2010 | Kanda | A61B 1/041 382/173 |
| 2010/0277650 A1* | 11/2010 | Matsuzaki | A61B 1/00009 348/700 |
| 2011/0255757 A1 | 10/2011 | Nishimura et al. | |
| 2011/0255758 A1 | 10/2011 | Nishimura et al. | |
| 2011/0255759 A1 | 10/2011 | Nishimura et al. | |
| 2011/0299748 A1 | 12/2011 | Nishimura et al. | |
| 2012/0002026 A1 | 1/2012 | Honda et al. | |
| 2012/0316421 A1* | 12/2012 | Kumar | A61B 1/00009 600/407 |
| 2013/0038711 A1* | 2/2013 | Sato | A61B 1/00048 348/68 |
| 2013/0152020 A1* | 6/2013 | Nishiyama | A61B 1/00009 715/835 |
| 2015/0187063 A1* | 7/2015 | Takahashi | A61B 1/00009 382/128 |
| 2016/0278743 A1* | 9/2016 | Kawashima | G01S 7/52033 |
| 2017/0004620 A1* | 1/2017 | Kitamura | A61B 5/02042 |
| 2017/0004625 A1* | 1/2017 | Kamiyama | G06T 7/0016 |
| 2017/0046825 A1* | 2/2017 | Xu | A61B 1/00009 |
| 2017/0231714 A1* | 8/2017 | Kosmecki | A61B 90/37 345/419 |
| 2017/0270363 A1* | 9/2017 | Polak | G06K 9/00758 |
| 2018/0060670 A1* | 3/2018 | Baker | G06K 9/6268 |
| 2018/0108138 A1* | 4/2018 | Kluckner | G06T 7/11 |

FOREIGN PATENT DOCUMENTS

| | | |
|---|---|---|
| JP | 2005348902 A | 12/2005 |
| JP | 2006223377 A | 8/2006 |
| JP | 2007175432 A | 7/2007 |
| WO | 2007135884 A1 | 11/2007 |
| WO | 2008139812 A1 | 11/2008 |

OTHER PUBLICATIONS

International Search Report (ISR) and Written Opinion dated Aug. 18, 2015 issued in International Application No. PCT/JP2015/064450.

* cited by examiner

FIG. 7
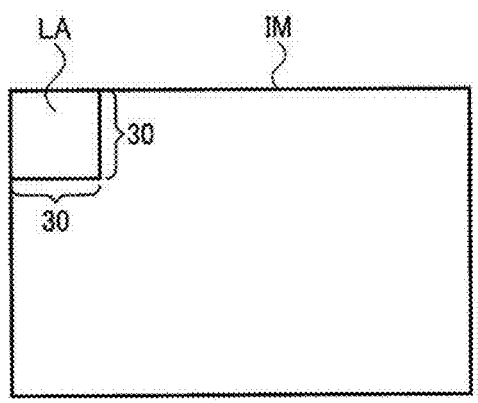
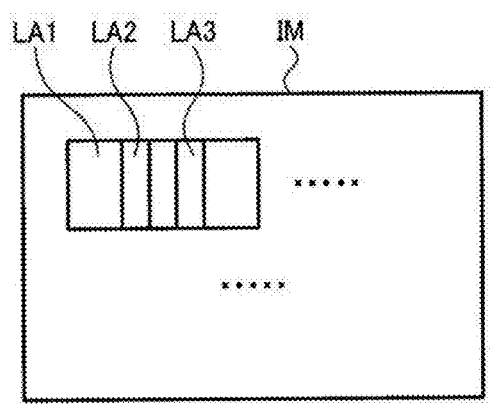
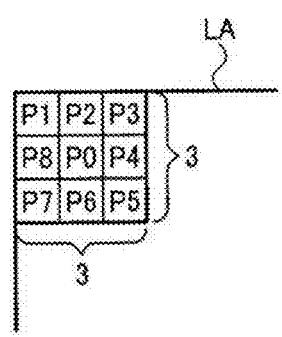
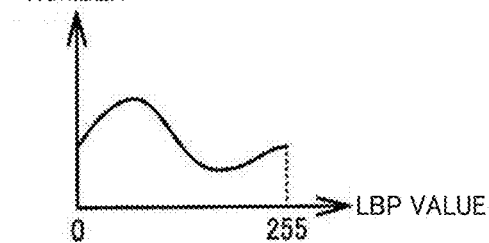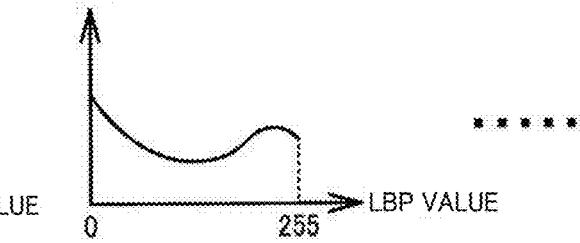

FIG. 11
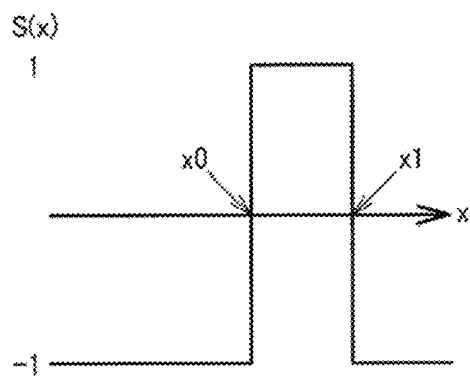
*
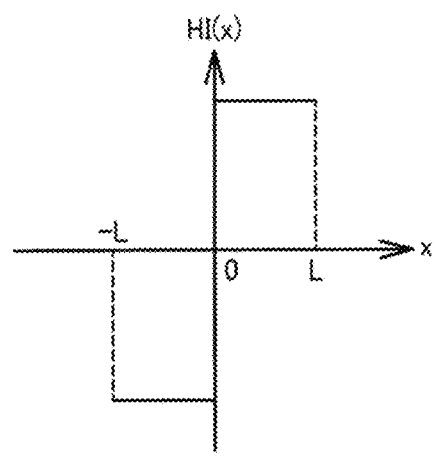
=
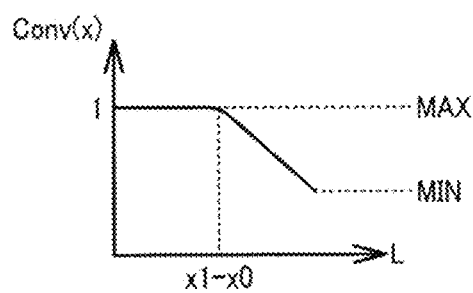

US 10,360,474 B2

IMAGE PROCESSING DEVICE, ENDOSCOPE SYSTEM, AND IMAGE PROCESSING METHOD

CROSS REFERENCE TO RELATED APPLICATION

This application is a continuation of International Patent Application No. PCT/JP2015/064450, having an international filing date of May 20, 2015, which designated the United States, the entirety of which is incorporated herein by reference. Japanese Patent Application No. 2014-129068 filed on Jun. 24, 2014 is also incorporated herein by reference in its entirety.

BACKGROUND

The present invention relates to an image processing device, an endoscope system, an image processing method, and the like.

There is a need for a technique that extracts a feature quantity from time-series images to implement scene classification, and calculates (determines) the scene change position. The scene classification process may be designed to detect a change in scene when a change from one state to another state has occurred. For example, such a scene classification process is used when the object (e.g., internal organ) change position is estimated from images captured using a capsule endoscope. For example, JP-A-2004-321603 and JP-A-2007-175432 disclose such a method.

The method disclosed in JP-A-2004-321603 calculates a red level and a blue level of an image, performs a low-pass filtering process in the time-axis direction to generate a graph of the red level and a graph of the blue level, detects a color change edge from each graph, and automatically determines the internal organ range from the temporal position of the color change edge.

The method disclosed in JP-A-2007-175432 performs a smoothing process using a filter having a specific size on a feature quantity in the time-axis direction to detect a change from the stomach to the small intestine. For example, a filter having a size of 20 (i.e., 20 images in the time-axis direction) is used as the filter having a specific size.

For example, a Gaussian filter represented by the following expression (1) is used as the low-pass filter in the time-axis direction.

$$\frac{1}{\sqrt{2\pi}\,\sigma}\exp\!\left(-\frac{x^2}{2\sigma^2}\right) \quad (1)$$

SUMMARY

According to one aspect of the invention, there is provided an image processing device comprising:
a processor comprising hardware,
the processor being configured to implement;
an image acquisition process that acquires time-series images that were captured in time series; and
a process that detects a change position, the change position being a position at which an object captured within the time-series images changes from a first object to a second object,
wherein the processor is configured to implement the process that extracts a feature quantity from each of the time-series images, determines whether the object captured within each of the time-series images is the first object or the second object based on the feature quantity, extracts candidate positions for the change position based on results of the determination, and compares the candidate positions based on the results of the determination to determine the change position.

According to one aspect of the invention, the object is determined based on the feature quantity extracted from the time-series images, and the candidate positions for the object change position are extracted from the time-series determination results, and compared to determine the object change position from the candidate positions. This makes it possible to improve the estimation accuracy with regard to the object change position.

According to another aspect of the invention, there is provided an endoscope system comprising:
the above image processing device; and
a capsule endoscope that captures the time-series images.

According to another aspect of the invention, there is provided an image processing method comprising:
acquiring time-series images that were captured in time series;
extracting a feature quantity from each of the time-series images;
determining whether an object captured within each of the time-series images is a first object or a second object based on the feature quantity;
extracting candidate positions for a change position based on results of the determination, the change position being a position at which the object captured within the time-series images changes from the first object to the second object; and
comparing the candidate positions based on the results of the determination to determine the change position.

BRIEF DESCRIPTION OF THE DRAWINGS

FIG. 7 is a view illustrating a local feature quantity.
FIG. 11 is a view illustrating a convolution that is performed while changing a window size L.

DESCRIPTION OF EXEMPLARY EMBODIMENTS

The exemplary embodiments of the invention are described below. Note that the following exemplary embodiments do not in any way limit the scope of the invention laid out in the claims. Note also that all of the elements described below in connection with the exemplary embodiments should not necessarily be taken as essential elements of the invention.

1. Basic Configuration Example

An example in which the internal organ change position is determined from images captured using a capsule endoscope is described below. Note that the embodiments of the invention are not limited thereto. For example, the embodiments of the invention may be applied to images captured using a scope-type endoscope apparatus or the like. The object for which the change position is determined may be an object that necessarily changes during imaging (in the imaging path). For example, the object for which the change position is determined may be an object (e.g., internal organ) of which the change position is fixed and necessarily exists instead of an object that changes unpredictably and frequently (e.g., change in scene).

It is possible to assist the doctor in making a diagnosis from images captured using a capsule endoscope by quickly presenting the images of the desired internal organ to the doctor. For example, the internal organ change position may be estimated from the images, and the images may be classified corresponding to the internal organ captured within each image (see JP-A-2004-321603 and JP-A-2007-175432).

However, the doctor may make a wrong diagnosis if the change position is inaccurately estimated. For example, when the doctor checks a lesion in the large intestine, an image that belongs to the large intestine, but has been erroneously determined to belong to the small intestine, is not presented to the doctor. When a lesion is captured within such an image, the doctor may miss the lesion.

The power supply capacity of a capsule endoscope is limited since a capsule endoscope is small. Therefore, only a specific internal organ may be intensely captured in order to reduce power consumption. For example, the imaging frequency is reduced in a region up to the small intestine, and is increased when it has been determined that the capsule endoscope has entered the large intestine. In this case, an increase in power consumption occurs if it is erroneously determined that a change from the small intestine to the large intestine has occurred before the actual change position is reached, and part of the large intestine is not captured if it is erroneously determined that a change from the small intestine to the large intestine has occurred after the actual change position has been reached.

Figure 1:
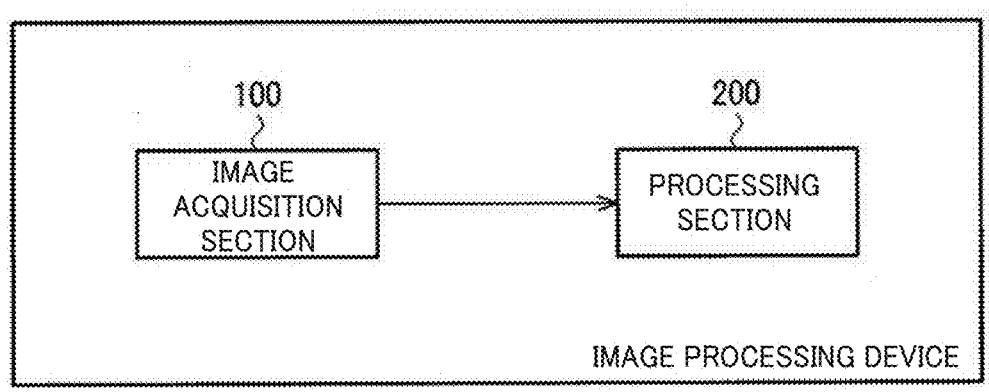
FIG. 1 illustrates a basic configuration example of an image processing device.

FIG. 1 illustrates a basic configuration example of an image processing device according to the embodiments of the invention that can solve the above problem. The image processing device includes an image acquisition section 100 that acquires time-series images that were captured in time series, and a processing section 200 that detects a change position, the change position being a position at which an object captured within the time-series images changes from a first object to a second object.

The processing section 200 extracts a feature quantity from each of the time-series images, and determines whether the object captured within each of the time-series images is the first object or the second object based on the feature quantity. The processing section 200 extracts candidate positions for the change position based on the results of the determination, and compares the candidate positions based on the results of the determination to determine the change position.

Figure 8:
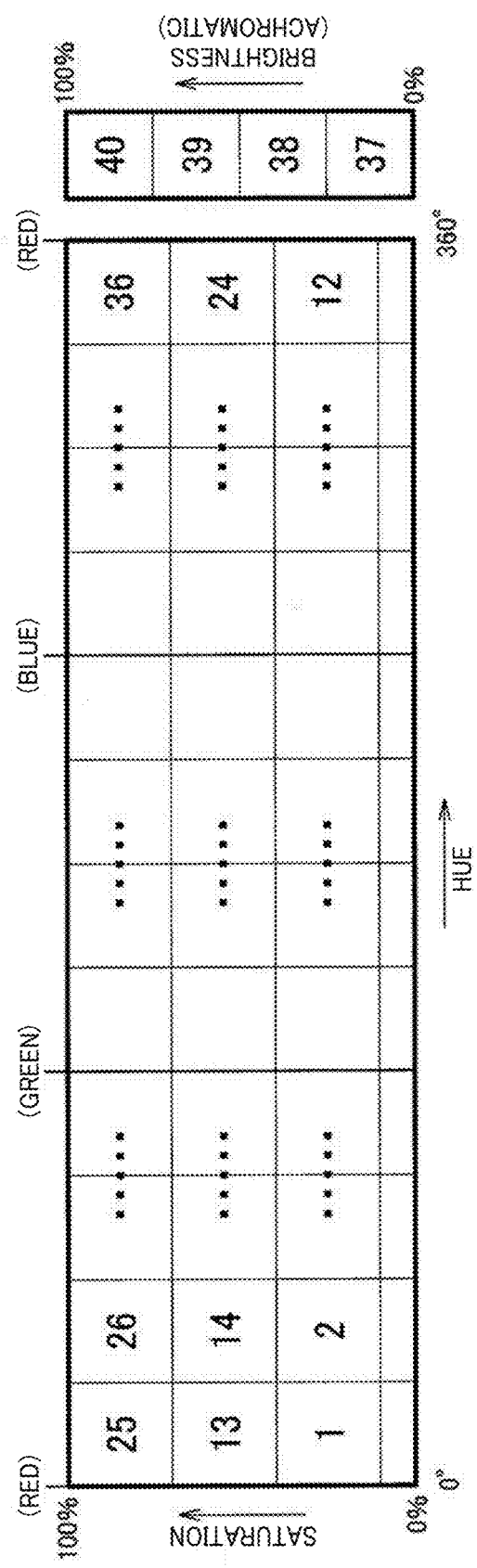
FIG. 8 is a view illustrating a local feature quantity with respect to a color.

For example, a learning process is performed in advance by means of a support vector machine (SVM) using labeled training images, and whether the object captured within each of the time-series images is the stomach or the small intestine is determined (classified) using the learned SVM (as described later with reference to FIGS. 3 to 6, for example). The candidate positions for the change position from the stomach to the small intestine are extracted using the degree of similarity between the time-series determination results and a step function (as described later with reference to FIGS. 7 to 9, for example). The candidate positions are compared based on the determination results to select an appropriate candidate position (final candidate position), and the final candidate position is output as the final change position (as described later with reference to FIGS. 10 to 12, for example).

The term "time-series images" used herein refers to images which were captured and are arranged in time series and for which the label is unknown. For example, the term "time-series images" used herein refers to video images, or images sequentially (consecutively) captured at given intervals. The time-series images may be images captured at indefinite (irregular) intervals. For example, the imaging interval of a capsule endoscope may be changed, or the time-series interval may change due to image summarization or the like. The position (change position and candidate position) corresponds to the number (frame number) of each of the images arranged in time series (with respect to the first image). In the example illustrated in FIG. 9, 10,000 images img00001 to img10000 are arranged in time series, and the number with respect to the first time-series image img00001 corresponds to the position x.

According to the embodiments of the invention, it is possible to determine an accurate change position with respect to the actual change point (position) by extracting the candidate positions for the change position using (from) the internal organ determination results, and determining the change position from the candidate positions. Specifically, when a low-pass filtering process is performed in the time-axis direction (see JP-A-2004-321603 and JP-A-2007-175432), the change edge of the determination results is shifted due to the effect (window size and half-width dependence) of the smoothing parameter σ and the like. Since the method according to the embodiments of the invention can prevent a situation in which such a shift in change edge occurs, it is possible to accurately detect the change position without being affected by the smoothing parameter σ and the like.

According to the embodiments of the invention, the processing section 200 calculates an evaluation value (MIN Conv(x) or MAX Conv(x)) by performing a convolution on the time-series determination results S(x) and a step function H(x) (as described later with reference to the expressions (2) and (3)). The processing section 200 extracts the candidate positions Pcan based on the evaluation value Conv(x).

For example, "1" is assigned to the image that has been determined to correspond to the small intestine, and "−1" is assigned to the image that has been determined to correspond to the stomach to obtain the time-series determination results S(x) (see FIG. 7). In this case, it is considered that the determination results S(x) change in a stepwise manner at the position x at which the object changes from the stomach to the small intestine. It is possible to evaluate the degree of similarity by performing a convolution on the determination results S(x) and the step function H(x), and extract the step-like change points as the candidate positions.

According to the embodiments of the invention, the processing section 200 performs a convolution on the time-series determination results S(x) while changing a window size L with respect to each of the time-series images to calculate the evaluation value corresponding to each of the time-series images, and extracts the candidate positions Pcan based on the evaluation value (as described later with reference to the expressions (2) and (3)).

Since the time-series determination results S(x) change in a complex manner (see FIG. 7), a step-like change may be observed at a position that differs from the correct answer change position. The window size L is the width of the position x for which the step function H(x) is defined. When a convolution is performed with respect to each position x while the window size L is fixed, a position x at which the degree of similarity with respect to the step function H(x) unexpectedly increases is observed. According to the embodiments of the invention, since a convolution is performed with respect to each position x while changing the window size L, it is possible to prevent a situation in which the degree of similarity with respect to the step function H(x) unexpectedly increases, and accurately extract the candidate positions for the change position.

According to the embodiments of the invention, the processing section 200 calculates the minimum value (MIN Conv(x)) or the maximum value (MAX Conv(x)) of the results of the convolution performed while changing the window size L to be the evaluation value. The processing section 200 extracts the candidate positions Pcan by comparing the evaluation value with a threshold value for the evaluation value.

When the minimum value is used as the evaluation value, the results of the convolution when the degree of similarity with respect to a step function is lowest while the window size L is changed, are used. This corresponds to finding a position at which the degree of similarity with respect to a step function is low. When a position at which the degree of similarity with respect to a step function is high (i.e., the minimum value is large) has been found, the position thus found can be extracted as the candidate position. This makes it possible to accurately extract a candidate position that is likely to be the actual internal organ change position.

When the maximum value is used as the evaluation value, the results of the convolution when the degree of similarity with respect to a step function is highest while the window size L is changed, are used. This corresponds to finding a position at which even a low degree of similarity with respect to a step function is observed. This makes it possible to suppress a situation in which the candidate positions for the change position are missed.

The image processing device may be configured as described below. Specifically, the image processing device may include a memory that stores information (e.g., a program and various types of data), and a processor (i.e., a processor comprising hardware) that operates based on the information stored in the memory. The processor performs an image acquisition process that acquires time-series images that were captured in time series, and a process that detects a change position, the change position being a position at which an object captured within the time-series images changes from a first object to a second object. The processor extracts a feature quantity from each of the time-series images, determines whether the object captured within each of the time-series images is the first object or the second object based on the feature quantity, extracts candidate positions for the change position based on the determination results, and compares the candidate positions based on the determination results to determine the change position.

The processor may implement the function of each section by individual hardware, or may implement the function of each section by integrated hardware, for example. The processor may comprise hardware, and the hardware may include at least one of a circuit that processes digital signal, and a circuit that processes analog signal, for example. The processor may be a circuit device (e.g. an integrated circuit, and the like) or a plurality of circuit devices that is/are implemented on a circuit board, or a circuit element (e.g. a registor, capacitor, and the like) or a plurality of circuit elements that is/are implemented on a circuit board, for example. The processor may implement the function of each section by individual hardware, or may implement the function of each section by integrated hardware, for example. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an ASIC. The processor may include an amplifier, a filter, or the like that processes analog signal. The memory may be a semiconductor memory (e.g., SRAM or DRAM), a register, a magnetic storage device (e.g., hard disk drive), or an optical storage device (e.g., optical disk device). For example, the memory stores a computer-readable instruction. Each section of the imaging device (i.e., the image processing device (e.g., the image processing device 100 illustrated in FIG. 6) included in the imaging device) is implemented by causing the processor to execute the instruction. The instruction may be an instruction included in an instruction set that is included in a program, or may be an instruction that causes a hardware circuit included in the processor to operate. Each section of the image processing device refers to the image acquisition section 100 and the processing section 200 illustrated in FIGS. 1 and 2.

The operation according to the embodiments of the invention is implemented as described below, for example. The processor acquires (reads) time-series images captured in time series using an imaging section from the memory, for example. The processor extracts a feature quantity from each of the time-series images, and stores the extracted feature quantity in the memory. The processor determines whether the object captured within each of the time-series images is the first object or the second object based on the feature quantity read from the memory, and stores the determination results in the memory. The processor extracts the candidate positions for the change position based on the determination results read from the memory, and stores the candidate positions in the memory. The processor compares the candidate positions read from the memory based on the determination results read from the memory to determine the change position, and stores the change position in the memory.

Each section of the image processing device according to the embodiments of the invention is implemented by a module of a program that operates on the processor. For example, the image acquisition section 100 is implemented by an image acquisition module that acquires time-series images that were captured in time series. The processing section 200 is implemented by a processing module that detects a change position, the change position being a position at which an object captured within the time-series images changes from a first object to a second object. The processing module extracts a feature quantity from each of the time-series images, determines whether the object captured within each of the time-series images is the first object or the second object based on the feature quantity, extracts candidate positions for the change position based on the determination results, and compares the candidate positions based on the determination results to determine the change position.

2. Processing Section

Figure 2:
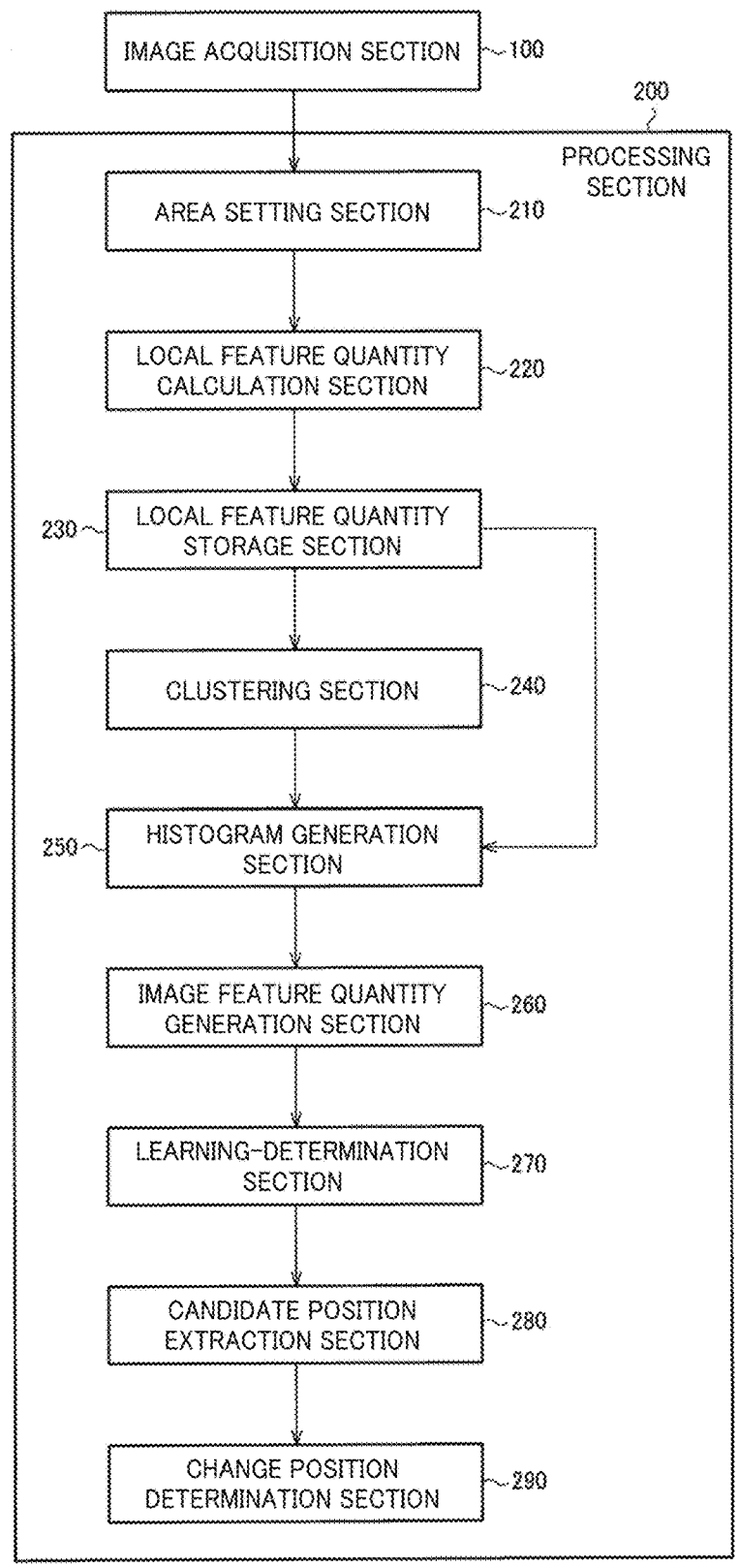
FIG. 2 illustrates a detailed configuration example of a processing section.

The embodiments of the invention are described in detail below. FIG. 2 illustrates a detailed configuration example of the processing section 200. The processing section 200 includes an area setting section 210, a local feature quantity calculation section 220, a local feature quantity storage section 230, a clustering section 240, a histogram generation section 250, an image feature quantity generation section 260, a learning-determination section 270 (learning-classification section), a candidate position extraction section 280, and a change position determination section 290.

The process according to the embodiments of the invention is described below with reference to the flowcharts illustrated in FIGS. 3 to 6. Note that an outline of the entire process is described below, and the details of each process are described later.

Figure 3:
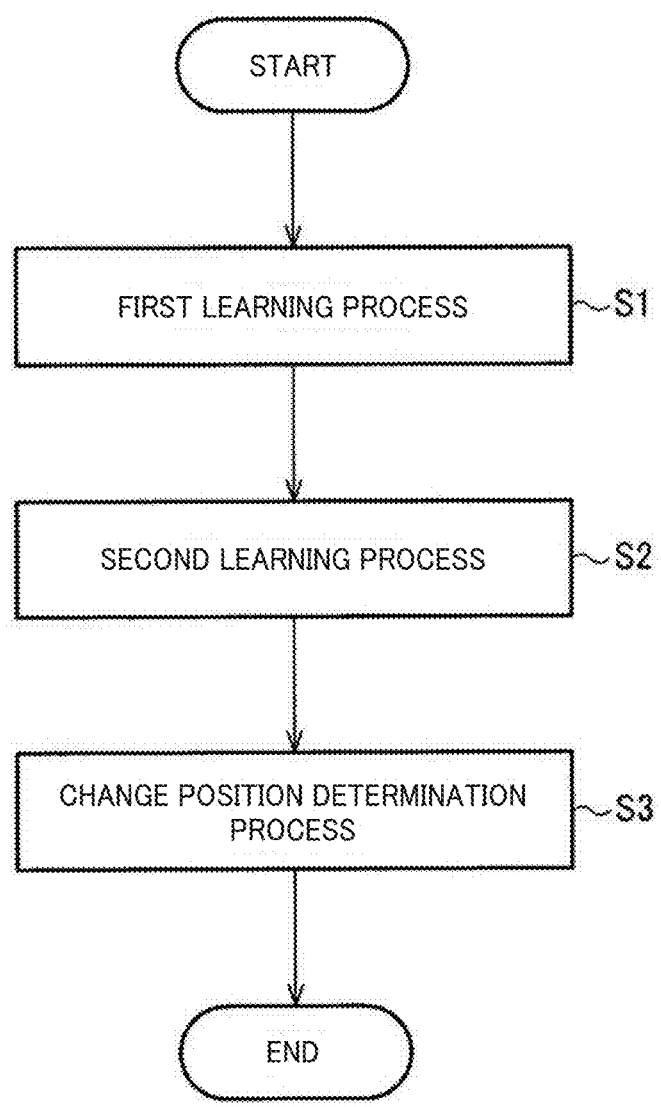
FIG. 3 illustrates a flowchart of a process according to the exemplary embodiments of the invention.

As illustrated in FIG. 3, the processing section 200 performs a first learning process (unsupervised learning) that extracts representative vectors from training images (step S1), and performs a second learning process that performs supervised learning using every feature quantity extracted from the correctly labeled training image using the representative vectors (step S2). The processing section 200 then performs a change position determination process that determines the internal organ change position from the time-series images obtained by capturing the inside of the body of the diagnosis target patient (step S3).

Figure 4:
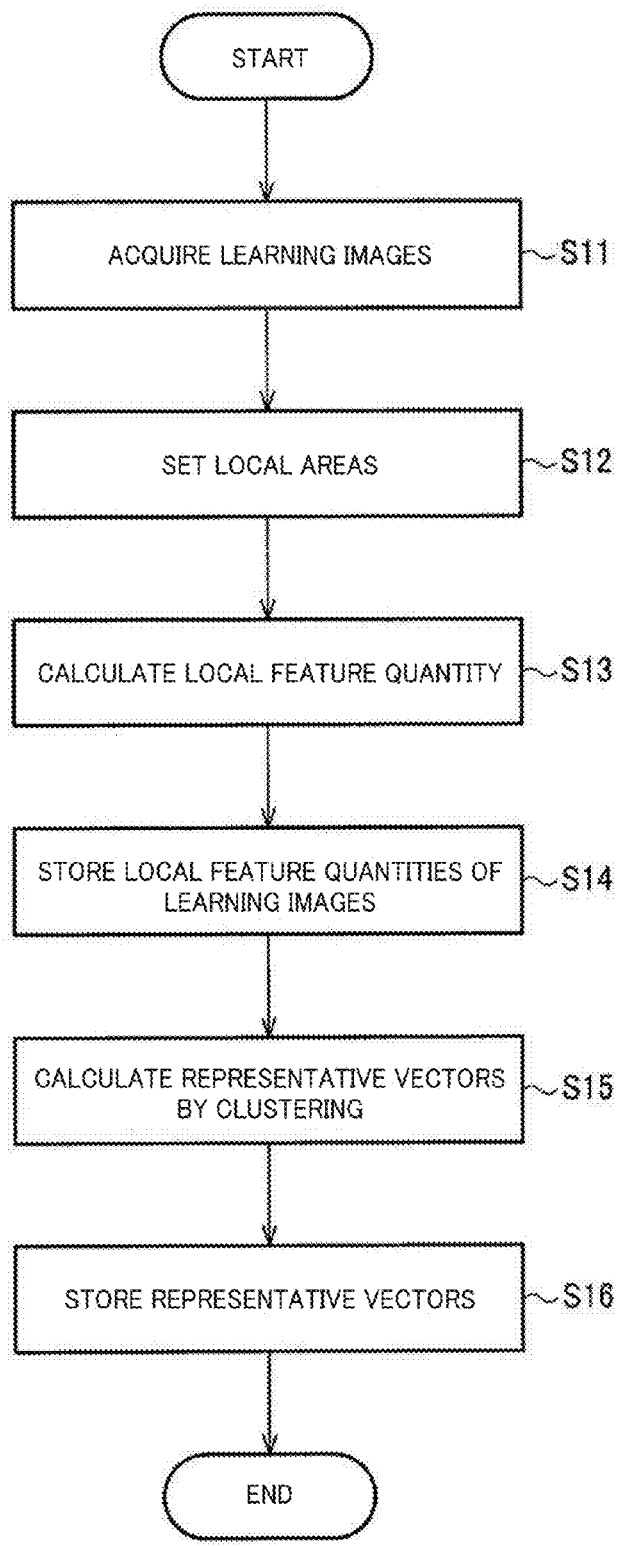
FIG. 4 illustrates a flowchart of a first learning process.

FIG. 4 illustrates a flowchart of the first learning process that is performed in the step S1. The image acquisition section 100 acquires a plurality of training images (step S11). The area setting section 210 sets a plurality of local areas to each of the plurality of training images (step S12). The local feature quantity calculation section 220 calculates a local feature quantity from each of the plurality of local areas (step S13). The local feature quantity storage section 230 stores the local feature quantity that has been calculated from each of the plurality of local areas set to each of the plurality of training images (step S14). The clustering section 240 clusters the local feature quantities stored in the local feature quantity storage section 230, and extracts the representative vectors (visual words) (step S15). The clustering section 240 stores the representative vectors in a storage section (not illustrated in the drawings) (step S16). The storage section in which the representative vectors are stored may be a memory that is included in the processing section 200, or may be a storage device that is provided outside the processing section 200, for example.

Figure 5:
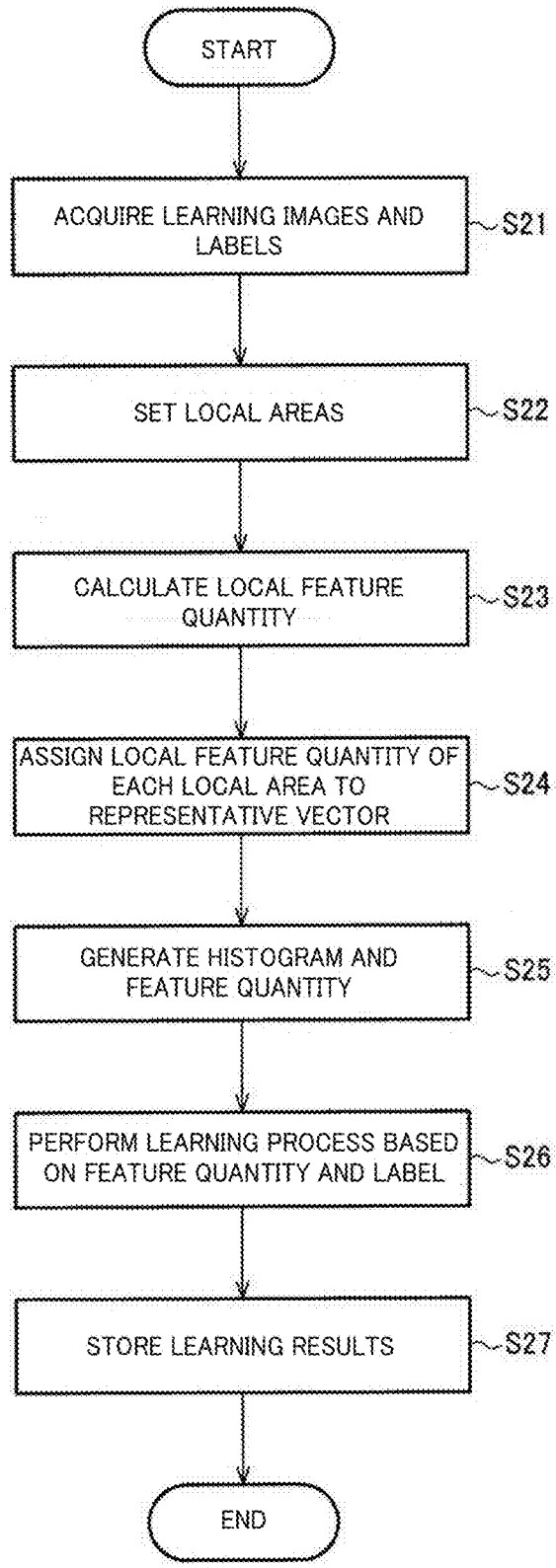
FIG. 5 illustrates a flowchart of a second learning process.

FIG. 5 illustrates a flowchart of the second learning process that is performed in the step S2. The image acquisition section 100 acquires a plurality of training images, and a label that corresponds to each of the plurality of training images (step S21). The label is information that represents the type of the internal organ that is captured within each image. The area setting section 210 sets a plurality of local areas to each of the plurality of training images (step S22), and the local feature quantity calculation section 220 calculates the local feature quantity from each of the plurality of local areas (step S23). The histogram generation section 250 calculates the representative vector that is closest to each local feature quantity, assigns the number of the representative vector to each local feature quantity, and counts the number of local feature quantities to which each number is assigned to generate a histogram. The image feature quantity generation section 260 generates a feature vector having each bin of the histogram as a component (step S25). The histogram and the feature vector are generated from each image. Specifically, the feature vector is a feature quantity that has been extracted from each image. The learning process is performed based on the feature vector and the label (step S26). The learning results are stored in a storage section (not illustrated in the drawings) (step S27). The storage section in which the learning results are stored may be a memory that is included in the processing section 200, or may be a storage device that is provided outside the processing section 200, for example.

Figure 6:
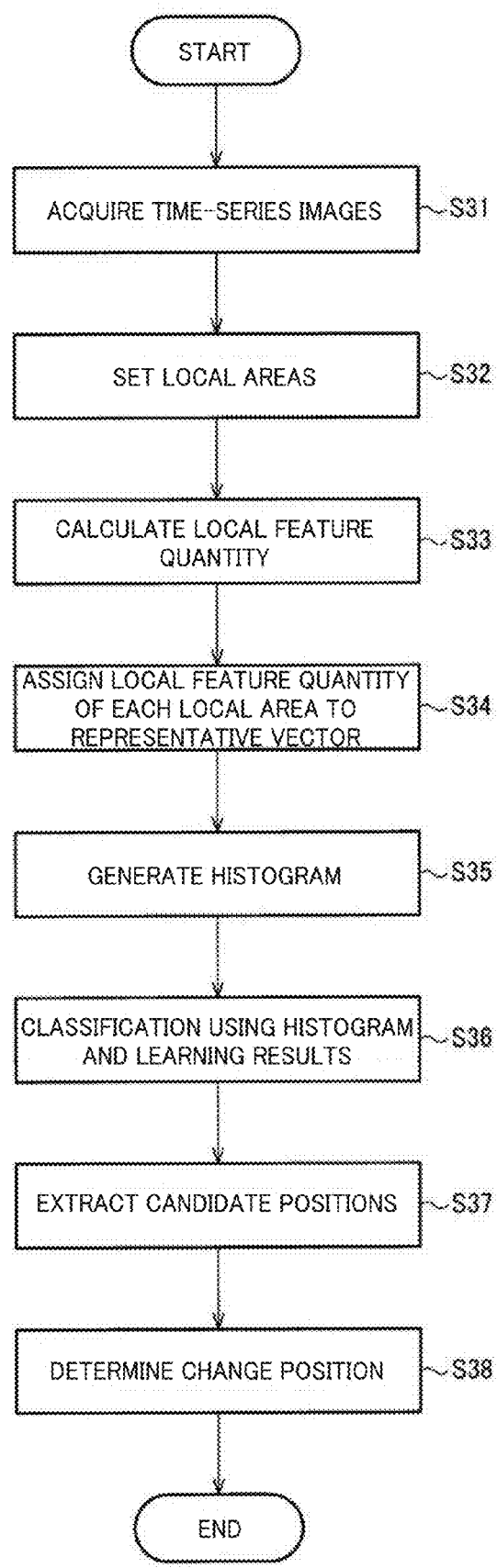
FIG. 6 illustrates a flowchart of a change position determination process.

FIG. 6 illustrates a flowchart of the change position determination process that is performed in the step S3. The image acquisition section 100 acquires the time-series images (step S31). The area setting section 210 sets a plurality of local areas to each of the time-series images (step S32), and the local feature quantity calculation section 220 calculates the local feature quantity from each of the plurality of local areas (step S33). The histogram generation section 250 calculates the representative vector that is closest to each local feature quantity, assigns the number of the representative vector to each local feature quantity, and counts the number of local feature quantities to which each number is assigned to generate a histogram. The image feature quantity generation section 260 generates a feature vector having each bin of the histogram as a component (step S35). The histogram and the feature vector are generated from each image. The learning-determination section 270 classifies the feature vector using the learning results (step S36). Specifically, the learning-determination section 270 determines the type of the internal organ that is captured within each image. The candidate position extraction section 280 extracts the candidate positions for the internal organ change position using the time-series determination results (S37). The change position determination section 290 compares the candidate positions to determine the internal organ change position (step S38).

3. Learning Process

Each process is described in detail below. The first learning process and the second learning process are performed as described below.

The training image that is acquired by the image acquisition section 100 is an image for which the relationship between the image and the type of internal organ (object) is known in advance. For example, an image obtained by capturing the inside of the body of a patient other than the diagnosis target patient is used as the training image. The plurality of training images need not be time-series images. The image acquisition section 100 corresponds to an interface section that receives an image captured by an imaging section, or a controller that reads an image stored in the image processing device, or reads an image stored in a storage device provided outside the image processing device, for example.

As illustrated in FIG. 7, the area setting section 210 sets a local area LA having a specific size to an image IM (one training image). More specifically, the area setting section 210 sets a plurality of local areas LA1, LA2, LA3, . . . so that the plurality of local areas LA1, LA2, LA3, . . . overlap each other. For example, when the image IM includes 288×288 pixels, the size of the local area is set to 30×30 pixels. Note that the size of the local area may be changed corresponding to the size of the image IM.

The local feature quantity calculation section 220 applies a local binary pattern (LBP) to the image within each local area LA, for example. The LBP value is calculated from 3×3 pixels within the local area LA. When the center pixel of the 3×3 pixels is referred to as P0, and the eight pixels situated around the pixel P0 are respectively referred to as P1 to P9, the pixel value of each of the pixels P1 to P9 is compared with the pixel value of the pixel P0, "1" is assigned to a pixel of which the pixel value is equal to or larger than that of the pixel P0, and "0" is assigned to a pixel of which the pixel value is smaller than that of the pixel P0. The bits assigned to the pixels P1 to P9 are arranged sequentially from the pixel P1 to the pixel P9 to obtain an 8-bit value. This process is performed corresponding to each pixel within the local area LA to obtain 900 (=30×30) LBP values per local area LA. The 900 LBP values are sorted according to their values (0 to 255), and counted to obtain a 256-dimensional local feature histogram that represents the local area LA. The 256-dimensional local feature histogram is used as a 256-dimensional feature vector (local feature quantity), and the feature vector is calculated corresponding to each of the local areas LA1, LA2, . . . to generate the feature vectors in the number of local areas.

The process that calculates the local feature quantity from the local area is performed on a plurality of images, and a number of vectors are stored in the local feature quantity storage section 230. For example, when the number of training images is 100, and 100 local areas are set to each training image, 10,000 feature vectors are stored in the local feature quantity storage section 230.

The clustering section 240 clusters the feature vectors stored in the local feature quantity storage section 230 using the K-means clustering method or the like, and extracts the representative vectors. The K-means clustering method sets the number of clusters (classes) to k, sets k representative vectors to an initial state, classifies the feature vectors into the k clusters, calculates the mean position of each cluster, moves the representative vectors, classifies the feature vectors into the k clusters, and repeats the above process to calculate the final classification. For example, the number k of representative vectors is set to 100. Note that the image within the local area that corresponds to the inverse map of the representative vector is referred to as "visual word" (i.e., visual dictionary).

The histogram generation section 250 searches the 100 representative vectors for a representative vector that is characterized in that the Euclidean distance between the local feature quantity and the representative vector is a minimum. The histogram generation section 250 performs this process on each local area in each image. The histogram generation section 250 assigns numbers 1 to 100 to the 100 representative vectors, and counts the number of local areas characterized in that the Euclidean distance with respect to each representative vector is a minimum, to generate a 100-dimensional histogram. The 100-dimensional histogram is generated from each training image. The 100-dimensional histogram is considered to be a 100-dimensional vector, and is referred to as a bag-of-features (BoF) feature vector of each image.

The image feature quantity generation section 260 generates the BoF feature vectors in the number of training images to generate a learning data set together with the correct answer label (e.g., the type of internal organ (e.g., stomach, small intestine, and large intestine)).

The learning-determination section 270 performs the learning process using the learning data set by means of a support vector machine (SVM), for example. The SVM is a learner that determines the label separating plane (e.g., a plane that separates the feature vector that corresponds to the stomach and the feature vector that corresponds to the small intestine) in the feature vector space from a learning data set. For example, a linear separation process is performed in the feature vector space to determine the separating plane. Alternatively, a linear separation process may be performed in a higher vector space to determine a separating plane that is nonlinear with respect to the dimensions of the feature vector.

Although an example in which one type of LBP local feature quantity is applied to each local area has been described above, another configuration may also be employed. For example, a scale-invariant feature transform (SIFT) may be used as a local feature quantity with respect to a gradient, or a local feature quantity with respect to a color (hue saturation value) may be used. Alternatively, the feature vector may be generated by applying a plurality of types of local feature quantities.

Methods that combine a color, a gradient, and a texture are roughly classified into an early fusion method that combines a color, a gradient, and a texture in an early stage of the process, and a late fusion method that combines a color, a gradient, and a texture in a late stage of the process.

Examples of the early fusion method include a method that represents a 3×3-pixel pattern within each local area using a uniform LBP (ULBP) feature quantity (texture feature quantity) and the HSV color feature of the center pixel. For example, the HSV color space is divided into 12 sections in the hue direction and 3 sections in the saturation direction, and the achromatic brightness is divided into 4 sections (see FIG. 8). In this case, the total dimensions of the feature quantity are 40. Since the dimensions of the ULBP feature quantity are 10, the dimensions of the resulting early fusion feature quantity are 400 (=40×10).

Examples of the late fusion method include a method that uses a joint histogram obtained by arranging the BoF histogram and the LBP histogram of the HSV color feature quantity as the feature vector of the image. Further examples of the late fusion method include a method that performs a learning process using a discriminator (e.g., SVM) (described later) with respect to only a color or a texture, or a combination thereof obtained by the early fusion method or the late fusion method, calculates the total classification score, and performs a determination process using a threshold value.

It is possible to provide a more accurate learner-classifier by combining the methods described above.

4. Change Position Determination Process

The change position determination process is described below.

The process that calculates the BoF feature vector is basically the same as described above in connection with the second learning process. Specifically, the image acquisition section 100 acquires the time-series images which were captured using a capsule endoscope and for which the label is unknown, the area setting section 210 sets a plurality of 30×30-pixel local areas to each of the time-series images so that the plurality of local areas overlap each other, and the local feature quantity calculation section 220 applies an LBP or the like to the image within each of the plurality of local areas to calculate a 256-dimensional feature vector. The histogram generation section 250 assigns the feature vector to the representative vector obtained from clustering to generate a 100-dimensional BoF feature vector from each image.

Note that a clustering process is not performed during the change position determination process since the representative vector obtained from clustering is used. Therefore, it suffices that the local feature quantities of at least one image be stored in the local feature quantity storage section 230 (i.e., the local feature quantities of a plurality of images need not necessarily be stored in the local feature quantity storage section 230).

The learning-determination section 270 determines a BoF feature vector for which the label is unknown using a learned SVM, and classifies the internal organ that is captured within each image. Since the input images are time-series images, time-series determination results are obtained accordingly.

The process that extracts the candidate positions for the internal organ change position from the time-series determination results is described below using an example in which the images are automatically classified into an image in which the stomach is captured and an image in which the small intestine is captured (i.e., binary image classification problem).

Figure 9:
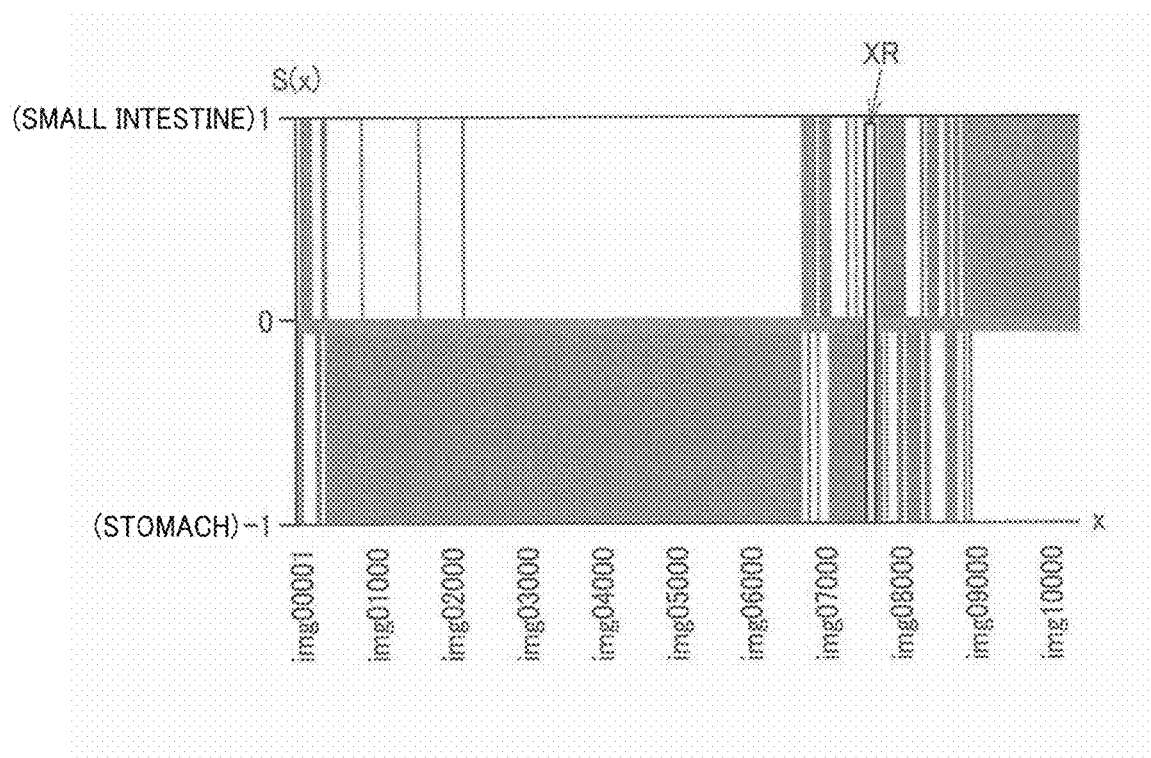
FIG. 9 illustrates an example of determination results.

FIG. 9 illustrates an example of the determination results when the time-series images are automatically classified into an image in which the stomach is captured and an image in which the small intestine is captured. The determination result $S(x)=-1$ represents that the stomach is captured in the image, and the determination result $S(x)=+1$ represents that the small intestine is captured in the image. Names (numbers) (img00001 to img10000) are sequentially assigned to the time-series images, and the determination results $S(x)$ are arranged in time series. The position x corresponds to the number of each time-series image. XR is the correct answer position (pylorus) at which the object changes from the stomach to the small intestine.

Figure 10:
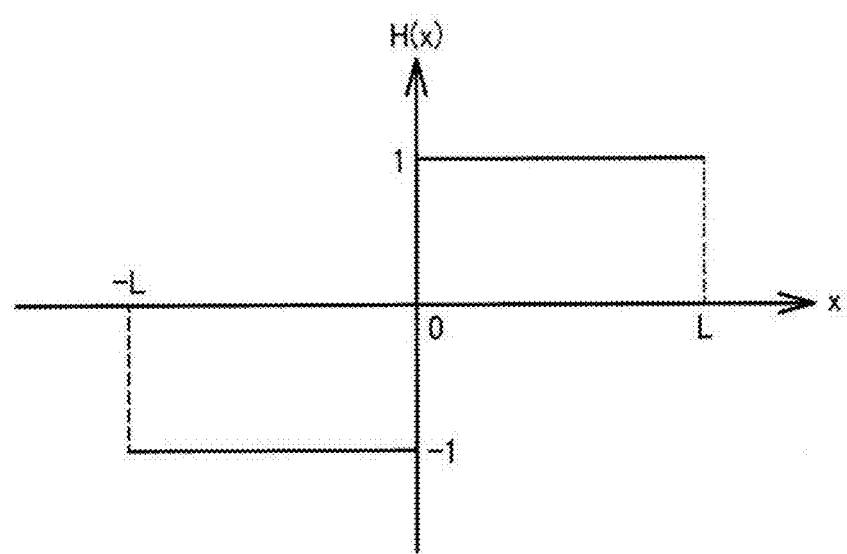
FIG. 10 is a view illustrating a step function.

The candidate position extraction section 280 performs a convolution on the determination results $S(x)$ and the step function $H(x)$ illustrated in FIG. 10 using the following expression (2), and calculates the candidate positions for the internal organ change position using the following expression (3).

$$\underset{L}{Conv}(x) = \frac{1}{2L}\sum_{y=-L}^{y=L} S(x-y)H(y) \quad (2)$$

$$Pcan = \underset{x}{Arg}\left[Th\left\{\underset{L=L0}{\overset{L=L1}{MIN}}\underset{L}{Conv}(x)\right\}\right] \quad (3)$$

The step function $H(x)$ is a function that is defined so that x is within the range from $-L$ to $+L$, and the window size L is variable. The expression (2) calculates the convolution value $Conv(x)$ while the window size L is fixed to an arbitrary value, and the value is divided (normalized) by 2L.

The part of the expression (3) in brackets "{ }" calculates the minimum convolution value $Conv(x)$ while the position x is fixed to an arbitrary value, and the window size L is changed from L0 to L1. For example, L0=10, and L1=MIN [x−M0, M1−x]. Note that M0 is the image search start position (e.g., M0=1), and M1 is the image search end position (e.g., M1=10,000).

FIG. 11 illustrates an example of the shape formed by the time-series determination results $S(x)$. When a convolution is performed at a position x0, the convolution value $Conv(x)$ is 1 when the window size L is equal to or smaller than (x1−x0) since the determination result $S(x)$ is a step function. When the window size L is larger than (x1−x0), the convolution value $Conv(x)$ decreases with respect to 1 since the degree of similarity between the shape formed by the determination results $S(x)$ and a step function decreases. Specifically, when the minimum convolution value $Conv(x)$ is used, the convolution value $Conv(x)$ when the degree of similarity with respect to a step function is lowest when the window size L is changed is selected.

Figure 12:
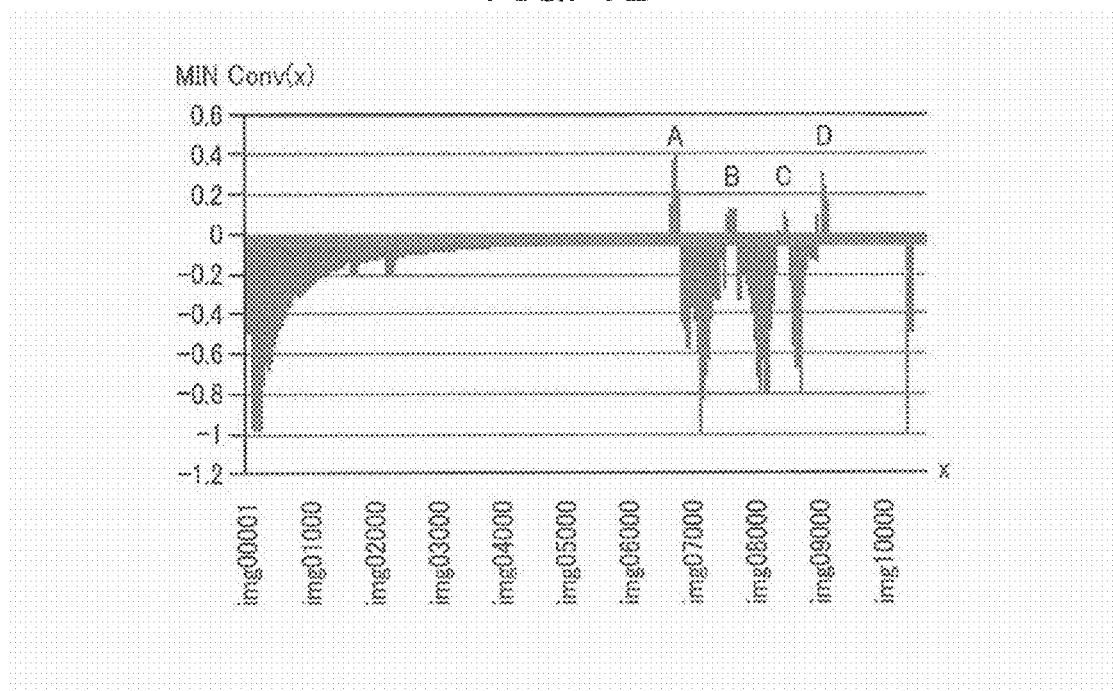
FIG. 12 illustrates an example of a minimum value obtained when a convolution was performed while changing a window size L.

The candidate position extraction section 280 calculates the minimum convolution value $Conv(x)$ at each position x between the search start position M0 and the search end position M1. FIG. 12 illustrates an example of the minimum convolution value $Conv(x)$. The part of the expression (3) in brackets "[ ]" implements a determination using a given threshold value by means of a Th (threshold value) function. The positions x at which the minimum convolution value $Conv(x)$ is equal to or larger than the threshold value are extracted as the candidate positions Pcan using the Arg function. For example, when the threshold value is 0, the positions A to D are selected to be the candidate positions Pcan in the example illustrated in FIG. 12.

Although an example in which the minimum convolution value is used has been described above, another configuration may also be employed. For example, the part of the expression (3) in brackets "{ }" may be changed to "MAX $Conv(x)$", and the maximum convolution value $Conv(x)$ while the window size L is changed from L0 to L1 may be used. In the example illustrated in FIG. 11, the maximum convolution value $Conv(x)$ is 1. When the maximum convolution value $Conv(x)$ is used, the convolution value $Conv(x)$ when the degree of similarity with respect to a step function is highest when the window size L is changed is selected.

The process that determines the final estimated position from the candidate positions A to D is described below.

For example, the change position determination section 290 focuses on the interval [A, B] between two adjacent points among the extracted candidate positions A to D, and compares the number of "+1" (small intestine) and the number of "−1" (stomach) within the interval. Specifically, the point A situated on the left side is determined to be the candidate point when the number of "+1" (small intestine) is larger than the number of "−1" (stomach), and the point B situated on the right side is determined to be the candidate point when the number of "+1" (small intestine) is equal to or smaller than the number of "−1" (stomach). This comparison process is continuously performed until the number of candidate positions reaches 1.

Figure 13:
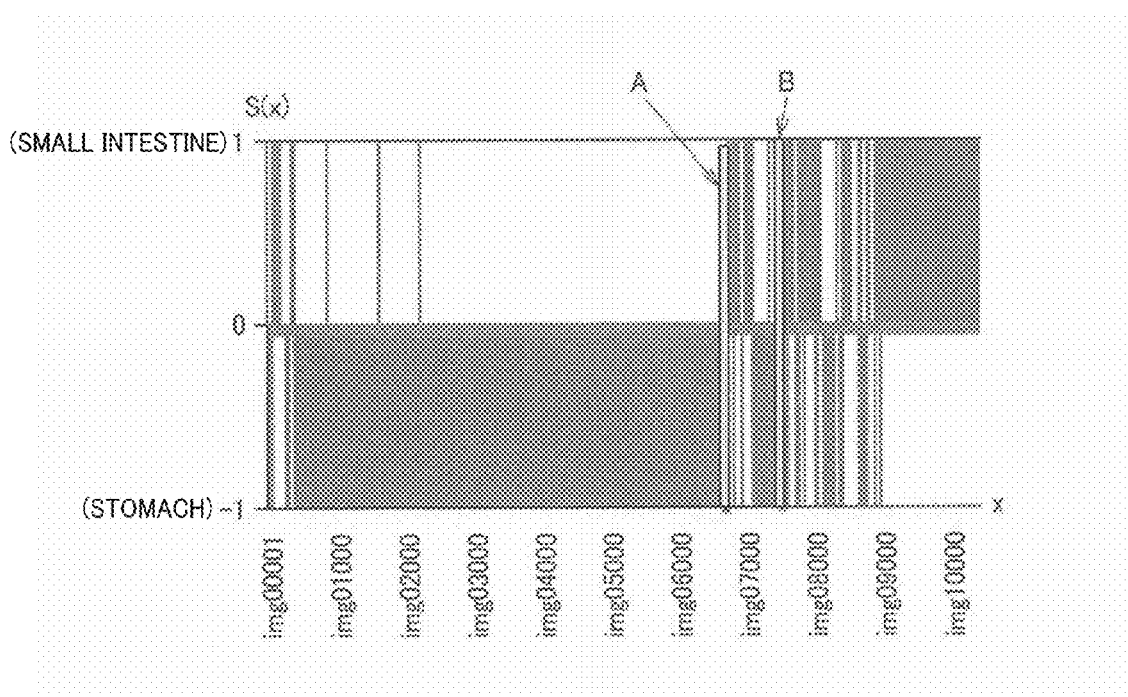
FIG. 13 is a view illustrating a change position determination process.
Figure 14:
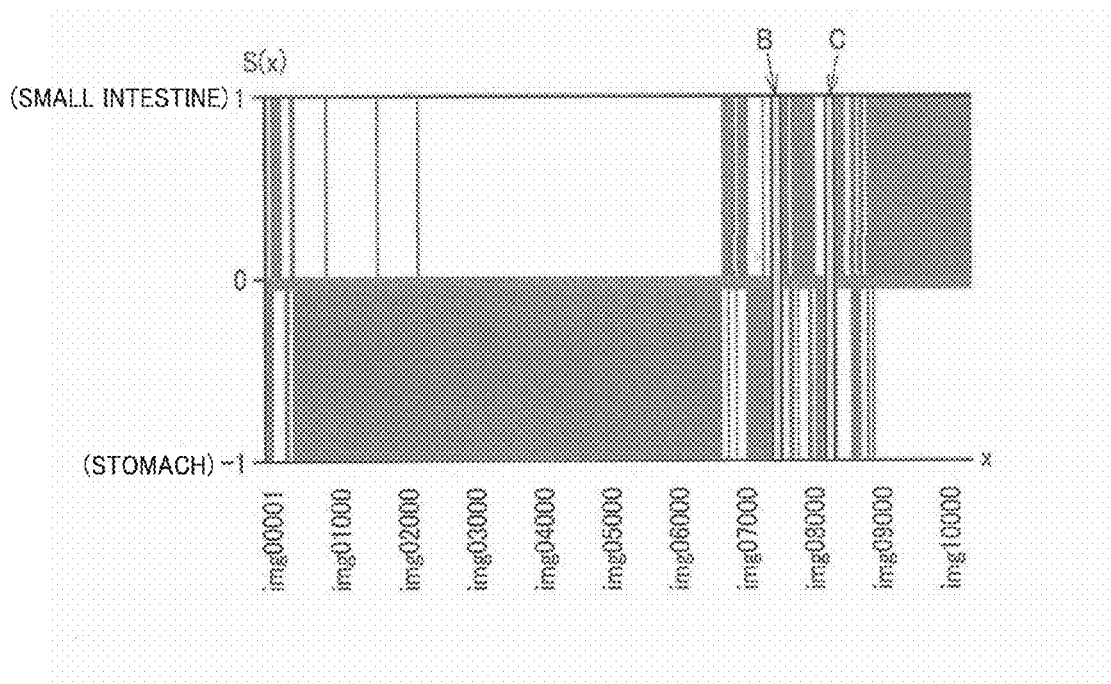
FIG. 14 is a view illustrating a change position determination process.
Figure 15:
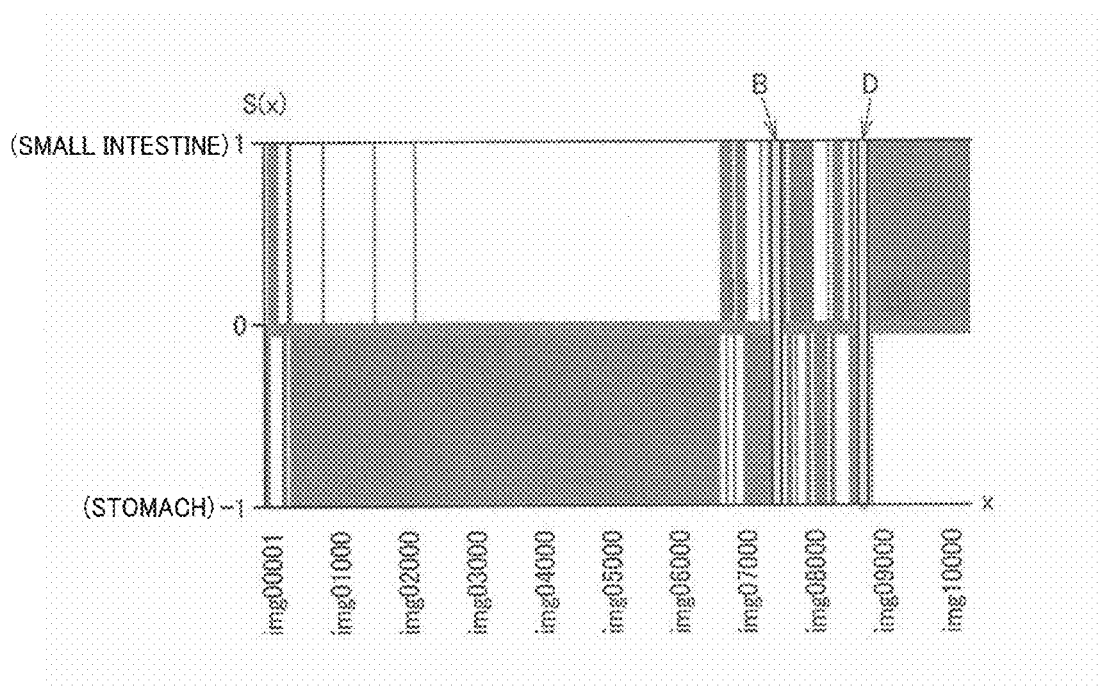
FIG. 15 is a view illustrating a change position determination process.

FIG. 13 is a view illustrating an example in which the number of "−1" and the number of "+1" are compared within the interval [A, B] between the candidate positions A and B according to the determination method described above. Since the number of "−1" is larger than the number of "+1" within the interval [A, B], the candidate position B is allowed to remain (i.e., the candidate position A is deleted from the processing target). The comparison process is then performed on the candidate positions B and C (see FIG. 14). Since the number of "+1" is larger than the number of "−1" within the interval [B, C], the candidate position B is allowed to remain (i.e., the candidate position C is deleted from the processing target). The comparison process is then performed on the candidate positions B and D (see FIG. 15). Since the number of "+1" is larger than the number of "−1" within the interval [B, D], the candidate position B is selected to be the final estimated position.

The selected position B approximately coincides with the correct answer position XR illustrated in FIG. 9. Specifically, it is possible to obtain a good estimation result by utilizing the above method.

According to the embodiments of the invention, when first to nth candidate positions (where n is a natural number equal to or larger than 2) have been extracted as the candidate positions, the processing section 200 selects an ith candidate position or a jth candidate position (where i and j are natural numbers that satisfy "i<j≤n") among the first to nth candidate positions based on the results of the determination between the ith candidate position and the jth candidate position.

For example, when the first to fourth candidate positions A to D have been extracted as described above with reference to FIG. 12, the first candidate position A or the second candidate position B is selected as described above with reference to FIG. 13 based on the determination results S(x) between the first candidate position A and the second candidate position B.

The candidate position is a position that has been determined to be close to the correct answer change position (i.e., a position at which the degree of similarity with respect to a step function is high) using the expressions (2) and (3). Specifically, the candidate position is a position that has been extracted without being affected by a low-pass filtering process and the like. It is possible to implement highly accurate estimation by selecting the change position from the candidate positions that have not been shifted due to a low-pass filtering process and the like. Since it is considered that the determination results between two candidate positions reflect the true change position, it is possible to select a candidate position that is closer to the correct answer change position by utilizing the determination results between two candidate positions.

According to the embodiments of the invention, when the object changes from the first object to the second object, the processing section 200 selects the jth candidate position when the number of results of the determination that the object is the first object is larger than the number of results of the determination that the object is the second object between the ith candidate position and the jth candidate position. The processing section 200 selects the ith candidate position when the number of results of the determination that the object is the second object is larger than the number of results of the determination that the object is the first object.

For example, when the object changes from the stomach (first object) to the small intestine (second object), and the number of determination results (−1) that the object is the stomach is larger than the number of determination results (+1) that the object is the small intestine between the first candidate position A and the second candidate position B (as described above with reference to FIG. 13), the second candidate position B is selected.

According to this configuration, it is possible to count the determination results between the ith candidate position and the jth candidate position, and estimate whether the ith candidate position or the jth candidate position is closer to the true change position based on the principle of majority rule. It is possible to estimate a candidate position among the first to nth candidate positions that is closest to the correct answer by repeating the above selection process.

According to the embodiments of the invention, the feature quantity is a feature quantity based on at least one of a local feature quantity with respect to a texture, a local feature quantity with respect to a color, and a local feature quantity with respect to a gradient. More specifically, the feature quantity is a feature quantity based on a combination of a local feature quantity with respect to a texture, and a local feature quantity with respect to a color, or a combination of the local feature quantity with respect to a texture, and a local feature quantity with respect to a gradient.

For example, a local feature quantity with respect to a texture is calculated by applying an LBP, a local feature quantity with respect to a color is calculated by dividing an HSV space, and a local feature quantity with respect to a gradient is calculated by applying a SIFT. The BoF feature vector (i.e., the feature quantity of the image) is calculated from these local feature quantities.

According to this configuration, it is possible to determine the internal organ that is captured within each image based on the features (e.g., texture, color, and gradient) of each image in which the internal organ is captured. Moreover, it is possible to improve the classification accuracy by combining a plurality of feature quantities. For example, when a significant difference is easily obtained corresponding to the type of internal organ by utilizing specific features in combination, it is possible to implement an accurate determination by utilizing such a combination.

According to the embodiments of the invention, the processing section 200 sets a plurality of local areas to each of the time-series images, calculates the local feature quantity with respect to each of the plurality of local areas, generates a histogram as the feature quantity, and determines whether the object is the first object or the second object based on the histogram and the results of learning performed in advance, the histogram being a histogram in which the local feature quantity is assigned to a representative vector among a plurality of representative vectors to which the local feature quantity belongs.

For example, the local feature quantity (e.g., LBP) is assigned to the representative vector calculated by the first learning process to generate a histogram of each image, and the histogram is used as the BoF feature vector (feature quantity) of each image. The BoF feature vector is classified into the stomach and the small intestine using the learned SVM.

According to this configuration, determination results represented by discrete values (e.g., binary values that respectively correspond to the stomach and the small intestine) can be obtained using a learner that has been subjected to a learning process using an image for which the correct answer label is known in advance. Therefore, it is possible to count the number of determination results corresponding to each internal organ, and compare the candidate positions as described above.

According to the embodiments of the invention, the image acquisition section 100 acquires a plurality of training images to which a label is assigned, the label representing whether the object is the first object or the second object. The processing section 200 performs the first learning process that calculates the local feature quantities from the plurality of training images, clusters the local feature quantities calculated from the plurality of training images, and generates a plurality of representative vectors. The processing section 200 performs the second learning process that calculates a histogram with respect to each of the plurality of training images based on the plurality of representative vectors, and performs a learning process based on the label assigned to each of the plurality of training images and the histogram.

For example, the type of internal organ (i.e., label) is linked to each image. The first learning process performs a clustering process on the local feature quantity (e.g., LBP) using the K-means clustering method. The second learning process performs an SVM learning process from the BoF feature vector calculated from the training image, and the internal organ label linked to the training image.

According to this configuration, it is possible to perform a clustering process by means of unsupervised learning to extract the representative vector, and perform a learning process by means of supervised learning that uses the BoF feature vector generated using the representative vector, and the correct answer label. The images which were obtained by capturing the digestive tract of the patient and for which the label is unknown, can be classified by utilizing the learner that has been subjected to the learning process.

5. Endoscope System

Figure 16:
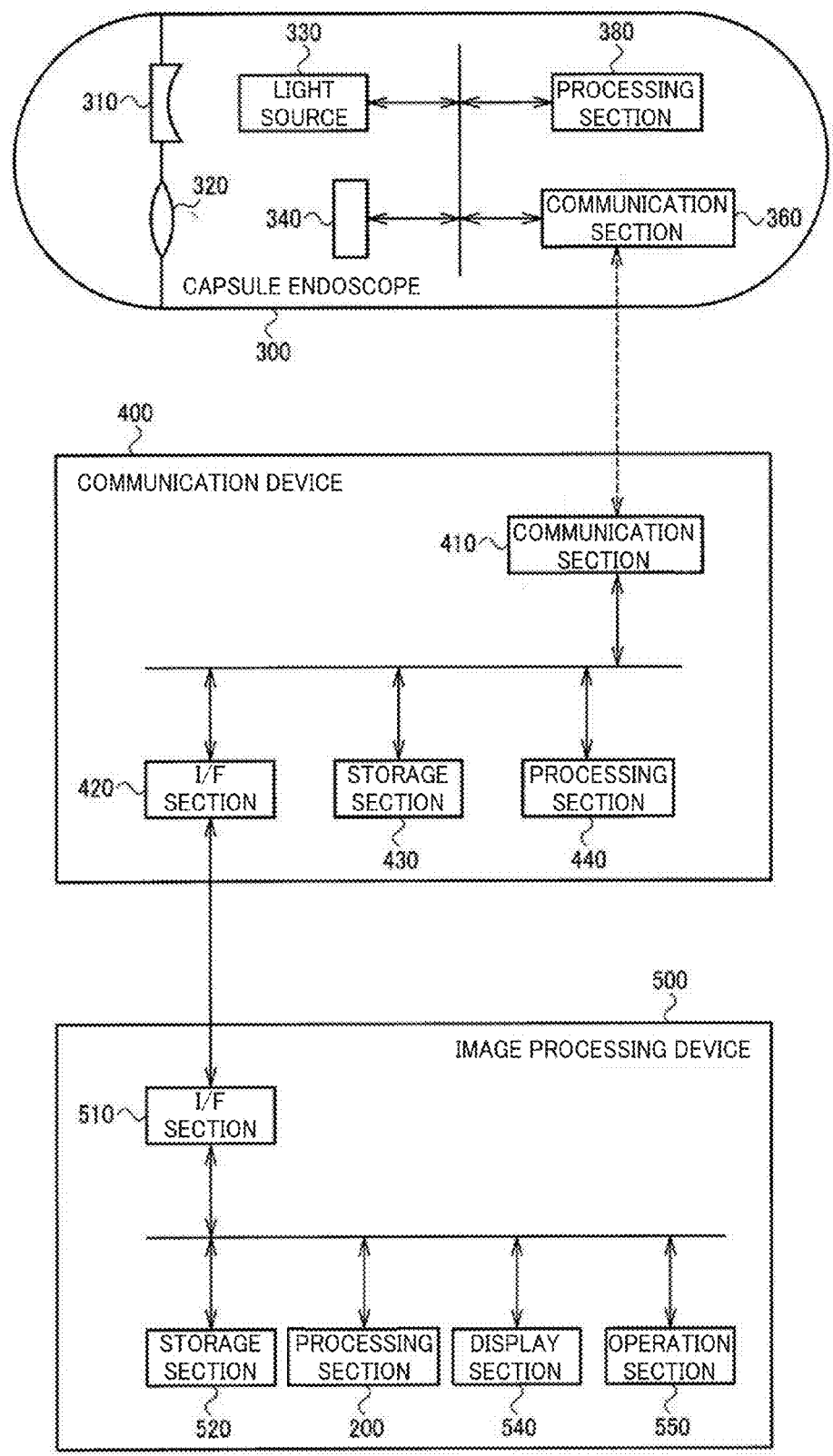
FIG. 16 illustrates a configuration example of an endoscope system.

FIG. 16 illustrates a configuration example of an endoscope system to which the image processing device according to the embodiments of the invention can be applied. The endoscope system includes a capsule endoscope 300, a communication device 400, and an image processing device 500.

The capsule endoscope 300 moves through the digestive tract of the patient who has swallowed the capsule endoscope 300, and sequentially captures the inside of the digestive tract. The capsule endoscope 300 includes a light source 330 that emits (generates) illumination light, a lens 310 that applies the illumination light to the digestive tract, a lens 320 that forms an image of the digestive tract, and an image sensor 340 that captures the image formed by the lens 320. The lens 320 and the image sensor 340 form an imaging section. The capsule endoscope 300 also includes a processing section 380 that controls each section of the capsule endoscope 300 (e.g., controls the imaging process), and a communication section 360 that communicates with the communication device 400 through wireless communication. The captured image is transferred to the communication device 400 through the communication section 360.

The communication device 400 includes a communication section 410 that communicates with the capsule endoscope 300 through an antenna attached to the abdomen or the like of the patient, a processing section 440 that controls each section of the communication device 400, and performs image processing and the like, a storage section 430 that stores an image and the like, and functions as a working memory for the processing section 440, and an I/F section 420 that performs an interface process with respect to an external device such as the image processing device 500. The captured image is transmitted to the image processing device 500 through the I/F section 420. The captured image may be transmitted after the imaging operation has been completed, or may be transmitted during the imaging operation.

The image processing device 500 performs a process that determines the internal organ change position (see above). For example, the image processing device 500 may be implemented by a general-purpose information processing device (e.g., PC), or may be implemented by a dedicated processing device. The image processing device 500 includes an I/F section 510 that performs an interface process with respect to the communication device 400, a processing section 200 that performs the process implemented by each section, image processing, the learning process, the change position determination process, and the like, a storage section 520 that stores an image and the like, and functions as a working memory for the processing section 200, a display section 540 that displays the captured image and the like, and an operation section 550 that is operated by the user.

The embodiments to which the invention is applied and the modifications thereof have been described above. Note that the invention is not limited to the above embodiments and the modifications thereof. Various modifications and variations may be made without departing from the scope of the invention. A plurality of elements described above in connection with the embodiments and the modifications thereof may be appropriately combined to implement various configurations. For example, some of the elements described above in connection with the embodiments and the modifications thereof may be omitted. Some of the elements described above in connection with different embodiments or modifications thereof may be appropriately combined. Specifically, various modifications and applications are possible without materially departing from the novel teachings and advantages of the invention. Any term cited with a different term having a broader meaning or the same meaning at least once in the specification and the drawings can be replaced by the different term in any place in the specification and the drawings.

What is claimed is:

1. An image processing device comprising:
a processor comprising hardware, the processor being configured to:
acquire time-series images that were captured in time series;
extract a feature quantity from each of the time-series images;
determine whether the object captured within each of the time-series images is a first object or a second object based on the feature quantity;
extract candidate positions for a change position based on results of the determination of whether the object is the first object or the second object, the change position being a position at which the object captured within the time-series images changes from the first object to the second object; and
compare the candidate positions to determine the change position based on the results of the determination of whether the object is the first object or the second object,
wherein the candidate positions are extracted by:
performing a convolution on time-series results of the determination of whether the object is the first object or the second object while changing a window size with respect to each of the time-series images to calculate an evaluation value corresponding to each of the time-series images; and
extracting the candidate positions based on the evaluation value.

2. The image processing device as defined in claim 1, wherein the processor is configured to:
calculate a minimum value or a maximum value of results of the convolution performed while changing the window size to be the evaluation value, and
extract the candidate positions by comparing the evaluation value with a threshold value for the evaluation value.

3. The image processing device as defined in claim 1, wherein, when first to nth candidate positions, where n is a natural number equal to or larger than 2, have been extracted as the candidate positions, the processor is configured to select, as the determined change position, an ith candidate position or a jth candidate position, where i and j are natural numbers that satisfy "i<j≤n", among the first to nth candidate positions based on the results of the determination of whether the object is the first object or the second object.

4. The image processing device as defined in claim 3, wherein, when the object changes from the first object to the second object, the processor is configured to select the jth candidate position when a number of results of the determination that the object is the first object is larger than a number of results of the determination that the object is the second object between the ith candidate position and the jth candidate position, and select the ith candidate position when the number of results of the determination that the object is the second object is larger than the number of results of the determination that the object is the first object between the ith candidate position and the jth candidate position.

5. The image processing device as defined in claim 1, wherein the feature quantity is a feature quantity based on at least one of a local feature quantity with respect to a texture, a local feature quantity with respect to a color, and a local feature quantity with respect to a gradient.

6. The image processing device as defined in claim 5, wherein the feature quantity is a feature quantity based on a combination of the local feature quantity with respect to a texture, and the local feature quantity with respect to a color, or a combination of the local feature quantity with respect to a texture, and the local feature quantity with respect to a gradient.

7. The image processing device as defined in claim 1, wherein the processor is configured to set a plurality of local areas to each of the time-series images, calculate a local feature quantity with respect to each of the plurality of local areas, generate a histogram as the feature quantity, and determine whether the object is the first object or the second object based on the histogram and results of learning performed in advance, the histogram being a histogram in which the local feature quantity is assigned to a representative vector among a plurality of representative vectors to which the local feature quantity belongs.

8. The image processing device as defined in claim 7, wherein the processor is configured to:
acquire a plurality of training images to which a label is assigned, the label representing whether the object is the first object or the second object,
perform a first learning process that calculates the local feature quantities from the plurality of training images, clusters the local feature quantities calculated from the plurality of training images, and generates the plurality of representative vectors, and
perform a second learning process that calculates the histogram with respect to each of the plurality of training images based on the plurality of representative vectors, and performs a learning process based on the label assigned to each of the plurality of training images and the histogram.

9. The image processing device as defined in claim 1, wherein the time-series images acquired by the processor are captured using a capsule endoscope.

10. An endoscope system comprising:
the image processing device as defined in claim 1; and
a capsule endoscope that captures the time-series images.

11. An image processing method comprising:
acquiring time-series images that were captured in time series;
extracting a feature quantity from each of the time-series images;
determining whether an object captured within each of the time-series images is a first object or a second object based on the feature quantity;
extracting candidate positions for a change position based on results of the determination of whether the object is the first object or the second object, the change position being a position at which the object captured within the time-series images changes from the first object to the second object; and
comparing the candidate positions to determine the change position based on the results of the determination of whether the object is the first object or the second object,
wherein the candidate positions are extracted by:
performing a convolution on time-series results of the determination of whether the object is the first object or the second object while changing a window size with respect to each of the time-series images to calculate an evaluation value corresponding to each of the time-series images; and
extracting the candidate positions based on the evaluation value.

* * * * *